United States Patent [19]

Haar et al.

[11] 4,329,062

[45] May 11, 1982

[54] POLYCHROMATIC PHOTOMETER

[75] Inventors: Hans-Peter Haar, Weilheim; Hermann Edelmann, D-Tutzing-Unterzeismering; Sigmar Klose, Berg, all of Fed. Rep. of Germany

[73] Assignee: Boehringer Mannheim GmbH, Mannheim-Waldhof, Fed. Rep. of Germany

[21] Appl. No.: 164,520

[22] Filed: Jul. 2, 1980

[30] Foreign Application Priority Data

Jul. 26, 1979 [DE] Fed. Rep. of Germany ....... 2930431

[51] Int. Cl.$^3$ ...................... G01N 21/13; G01N 21/27
[52] U.S. Cl. ................................... 356/414; 356/418; 250/205
[58] Field of Search ............... 356/414, 418, 419, 426, 356/427; 250/205

[56] References Cited

U.S. PATENT DOCUMENTS

| | | | |
|---|---|---|---|
| 3,504,981 | 4/1970 | Malvin | 356/418 X |
| 3,532,434 | 10/1970 | Jones, Jr. et al. | 250/205 X |
| 3,609,047 | 9/1971 | Marlow | 356/434 |
| 3,833,304 | 9/1974 | Liston | 356/418 X |
| 3,859,539 | 1/1975 | Allington | 250/205 X |
| 4,090,791 | 5/1978 | Siddigi et al. | 356/414 |

*Primary Examiner*—F. L. Evans
*Attorney, Agent, or Firm*—Toren, McGeady & Stanger

[57] ABSTRACT

In a polychromatic photometer a sample wheel containing angularly spaced sample compartments and a filter wheel containing angularly spaced filters are rotated by a common drive arrangement so that the sample compartments and filters are in turn rotated through and aligned with the optical path of a photometric measuring device. The number of sample compartments is different from the number of filters. The number of sample compartments and the number of filters are not evenly divisible by a common integer. The ratio of the angular velocity of the sample wheel to the angular velocity of the filter wheel is substantially equal to the ratio of the number of filters to the number of sample compartments.

15 Claims, 3 Drawing Figures

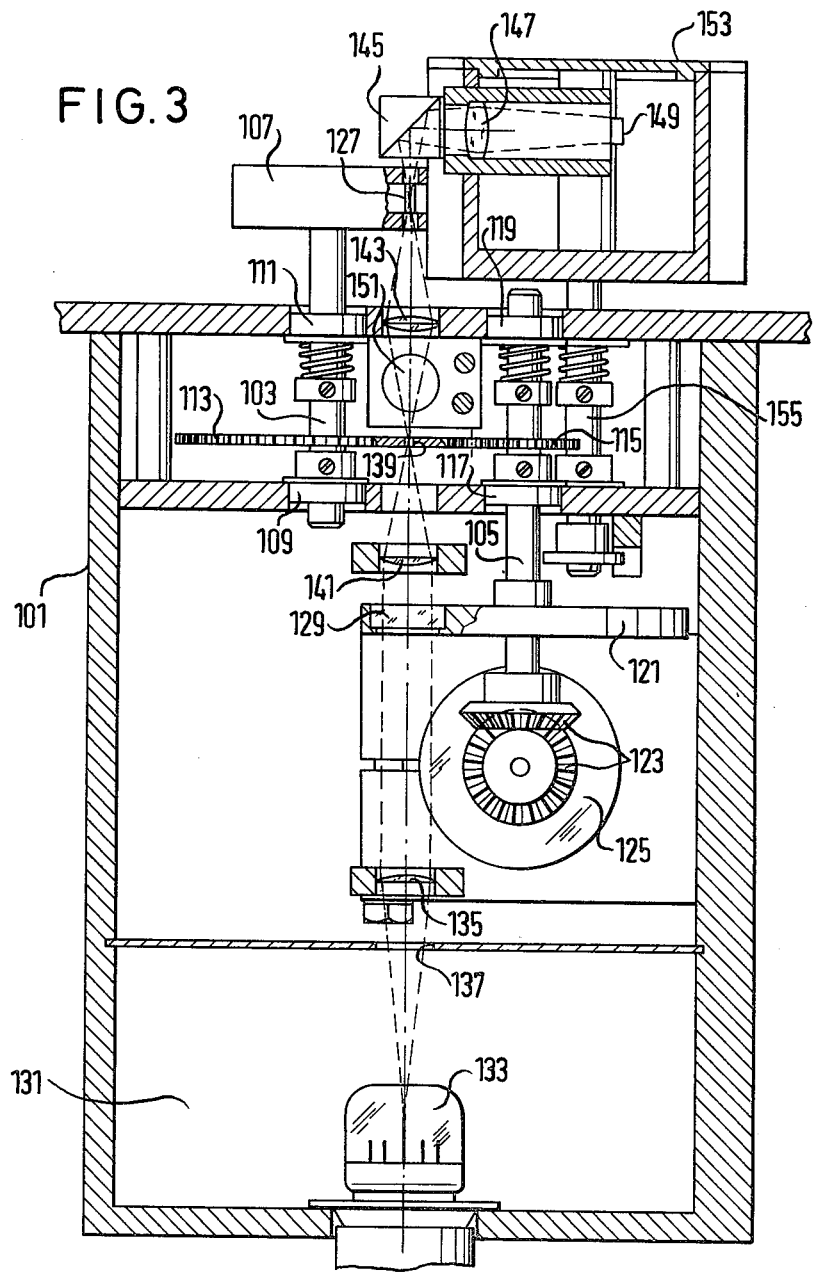

POLYCHROMATIC PHOTOMETER

SUMMARY OF THE INVENTION

The invention relates to a polychromatic photometer having a sample wheel containing a number of sample compartments spaced equiangularly apart around a circle. Samples to be checked can be placed in the compartments. A filter wheel spaced from the sample wheel has a number of filters spaced equiangularly apart around a circle. Each of the sample wheel and filter wheel rotates about a different axis which extends normally to the plane of the circle and through the center of the circle within the respective wheel. As the sample wheel and filter wheel are rotated, the sample compartments and the filters are moved one after the other into the optical path of a photometric measuring device.

A photometer of this type is known from "American Laboratory", February 1979, pages 19-28. The sample wheel is of the centrifugal type and is driven by a motor at a speed so that the samples, filled into the compartments of the sample wheel, completely fill the outer radial area of the compartments due to centrifugal force. The filter wheel is adjusted by a separate motor based on a preset program of a microcomputer.

Using this known photometer, the samples can be examined one after the other at different light wave lengths as determined by the filters in the filter wheel. It is important, however, in many instances that these examinations are performed as quickly as possible. In German Offenlegungsschrift No. 27 40 724 a polychromatic photometer is disclosed which meets this time requirement by separating light by means of a slit diaphragm into spectral portions as it emerges from the sample compartment and the intensity of the portions is simultaneously measured by a number of photo-detectors. While the advantage of fast measurements of the spectral portions is attained it is counterbalanced by the relatively high expenditure for the photo-detectors.

Therefore, it is the primary object of the present invention to provide an arrangement for reducing the time required for the examination of samples at different light wave lengths in a polychromatic photometer having a relatively limited production cost and arranged for the examination in series of several samples.

In accordance with the present invention, starting with the photometer described above, a driving device is provided which continuously rotates both the sample wheel and the filter wheel. The ratio of the angular velocity of the sample wheel to the angular velocity of the filter wheel is equal to the ratio of the number of filters to the number of samples. Further, the number of samples or sample compartments and the number of filters do not have a common integral divider.

In carrying out the photometric examination, each sample exactly coincides in the course of one cycle with each filter in alignment with the optical path of the photometric measuring device. The duration of the cycle, which results from the number of different combinations of samples and filters, is only insignificantly affected by the time intervals as the sample wheel and filter wheel move the portions of the wheels located between the samples and the filters.

The sample wheel and the filter wheel can be driven by separate motors as long as it is made certain that their rotational movements are synchronized in the cycle. This is most easily achieved using electric stepping motors. In a preferred embodiment, however, the sample wheel and the filter wheel are coupled together by a mechanical gear system and are driven by common motor. The gearing system provides the required synchronization with a uniform angle. The drive motor may also be an electric stepping motor.

In a relatively simple gearing system, the drive motor can drive the filter wheel directly with the gearing being provided between the filter wheel and the sample wheel. The diameter of the gear wheels is relatively large. The gear wheels should not project into the optical path of the photometric measuring device, and the diameter of the filter wheel and in particular of the sample wheel should not be too large because of the centrifugal forces occurring during rotation. Accordingly, an embodiment is provided in which the gearing system includes a driving shaft, a driven shaft and an intermediate shaft which is coupled to be driven by the driving shaft via gear members and with the intermediate shaft being coupled to the driven shaft by a belt drive. The gear members consist of a gear wheel secured on the driving shaft and another gear wheel which meshes with it and which is secured on the intermediate shaft. The belt drive, preferably a gear-belt drive, extends past the driving shaft, located near the driven shaft so that the filter wheel along with the sample wheel can project into the optical path of the photometric measuring device. In practice, the belt drive can have a gear ratio of 1:1.

It is unnecessary to use the belt drive between the intermediate shaft and the driven shaft when the gear wheel or wheels of the gearing system extend into the optical path of the photometric measuring device and are provided with passages for light at the areas aligned with the sample compartments in the sample wheel and with the filters in the filter wheel which are alignable in the optical path. As long as the number of light passages, arranged on a circle around the gear wheel shaft, is small, no problems result. As the number of light passages increases, however, the cross-section of the gear wheel between the light passages may become so small that the strength of the wheel suffers. Therefore, in a preferred embodiment, a photometric measuring device is used which has an optical system producing an intermediate image within the range of the light passages. Due to the provision of the intermediate image, the size of the light passages can be considerably reduced, so that a large number of the light passages can be provided through the gear wheel located adjacent one another without impairing the mechanical strength of the wheel. In its simplest embodiment, the gearing system includes two rotating shafts arranged parallel to the optical axis or path of the photometric measuring device. One shaft mounts the sample wheel and one of the gear wheels, the other shaft carries the filter wheel and the other gear wheel with the gear wheels being in meshed engagement. Usually more sample compartments are provided than filters, accordingly, the light passages are provided in the gear wheel mounted on the same shaft as the sample wheel.

Preferably, the axes of rotation of the sample wheel and filter wheel extend vertically with the sample wheel positioned above the filter wheel so that the samples can be filled into the compartments without any interference from the filter wheel.

The simplest possibility for indexing the combinations of the samples and the filters is to assign a counter to the sample wheel and to the filter wheel which count the number of rotations at each cycle. These counters may be electrical counters whose maximum counting capability is equal to the number of samples or filters.

The starting signal of the photo-receiver of the photometric measuring device, located in the optical path, depends essentially on the spectral emission characteristic of the light source, the degree of transmission of the individual filters, and its own spectral sensitivity characteristic. The photo-receiver, however, has a limited dynamic range which must be maintained during the measuring operation if the measuring error is to remain as small as possible. To assure that the photo-receiver continues to operate in its optimum dynamic range, preferably the photometric measuring device utilizes a flash light as the light source operated by an electrical energy source of controllable power with a control device adjusting the power of the energy source independently of the rotational position of the filter wheel.

For each filter in the filter wheel, the control element has a setting member at which the power of the energy source assigned to each filter can be set. The characteristics of the flash light, however, can change during its service life so that the setting members must again be adjusted. To automate the adjusting process in a photometric measuring device having a reference channel measuring the intensity of the light before it passes through the samples, the control element can be provided with a desired-value storage for the signals of the reference channel assigned to the individual filters of the filter wheel for determining the power of the energy source. During start up of the photometer and during the first rotation of the filter wheel, these desired-value signals are stored.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

BRIEF DESCRIPTION OF THE DRAWING

In the Drawing:

FIG. 3 is a schematic sectional view through the mechanical structure of a second embodiment of a polychromatic photometer incorporating the present invention.

DETAIL DESCRIPTION OF THE INVENTION

Figure 1:
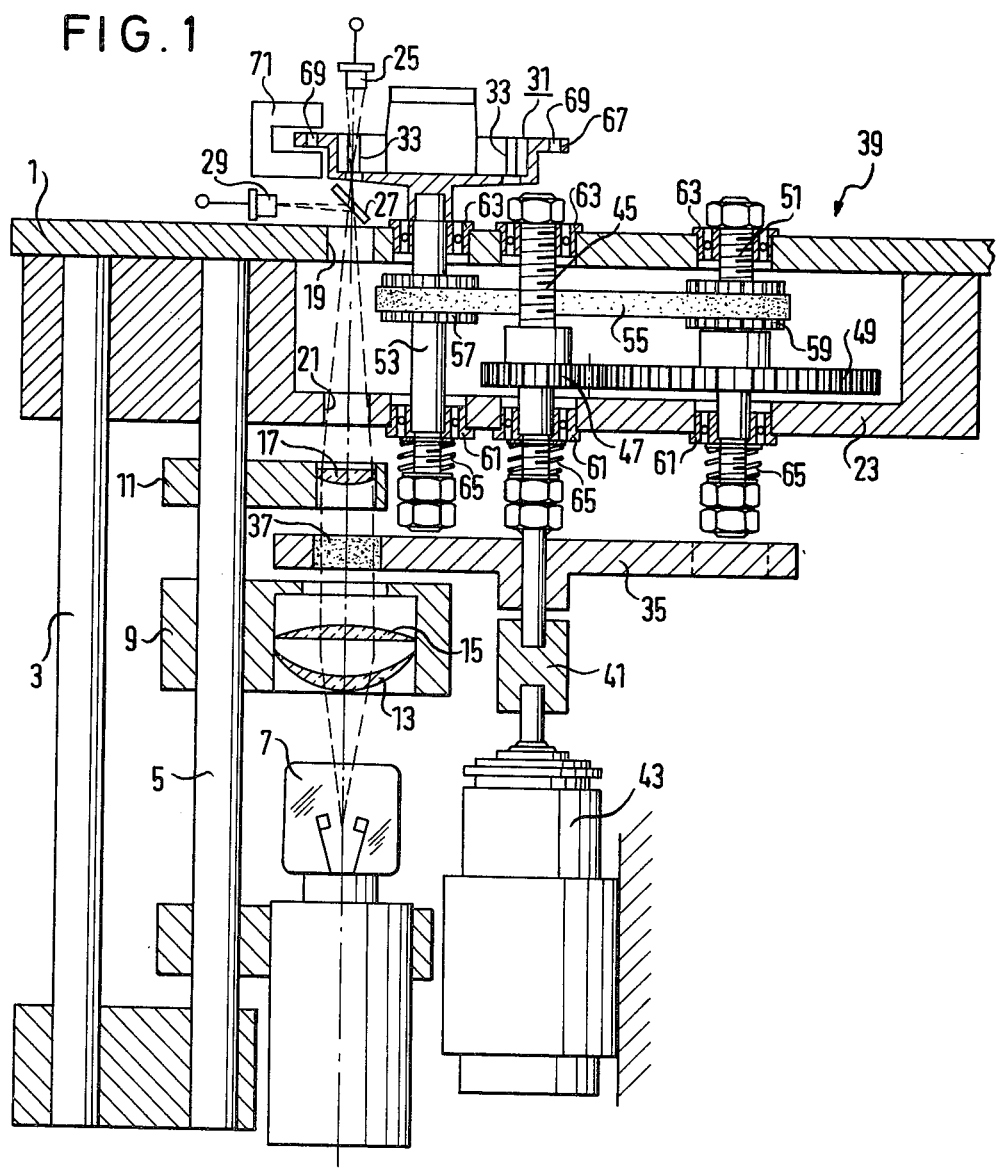
FIG. 1 is a schematic sectional view through the mechanical structure of a first embodiment of a polychromatic photometer incorporating the present invention.

In FIG. 1 a horizontal base plate 1 has a frame 3 and a guide member 5 extending vertically downwardly from the underside of the plate. A flash lamp 7 is mounted adjacent the lower end of the guide member 5 and two lens carriers 9 and 11 are positioned above the lamp and below the base plate 1. The lens carriers are adjustably mounted on the guide member 5 relative to one another, as in an optical bench. Lens carrier 9 contains condensing lenses 13, 15 while the lens carrier 11 has a collecting lens 17 for focusing the parallel beams coming from the condensing lenses 13, 15 at a location positioned above the base plate 1. Above the collecting lens 17, the light beams pass through openings 19, 21 in the base plate 1 or gear housing 23 connected to and extending downwardly from the base plate. Above the base plate the light beams are absorbed by the photo-detector 25 located along the optical axis of the photometer. Between the upper surface of the base plate 1 and the photo-detector 25, a beam splitter 27 is positioned in the optical path for deflecting a part of the light beams to a reference photo-detector 29 located laterally outwardly of the optical path. Located in the focal plane of the collecting lens 17 is a sample wheel 31 rotatable about a vertical axis and containing a number of sample compartments 33. The compartments 33 are equiangularly spaced apart about a circle concentric to the axis of the wheel. The samples to be examined are located in the compartments 33. While the sample wheel 31 is located above the base plate 1, a filter wheel 35 is positioned below the base plate between the lens carriers 9, 11. A number of filters 37 are located in the filter wheel 35 equiangularly spaced apart around a circle centered about the axis of rotation of the wheel. Each of the filters 37 has a different transmission wave length. Accordingly, samples in the compartments 33 can be photometrically measured at different wave lengths in accordance with the position of the filter wheel 35. The photo-detector 25 affords a signal proportional to the light intensity present after the light beam has passed through the sample located on the optical path. The signal of the reference photo-detector 29, proportional to the intensity of the light beam before entering the sample is, as is usual, utilized for eliminating intensity fluctuations of the light source.

Sample wheel 31 is coupled at a uniform rotation angle with the filter wheel 35 via gearing system 39. An electric motor 43 coupled directly to the filter wheel 35 by a coupling 41 drives the filter wheel and the sample wheel coupled to it at a uniform speed. The ratio of the speed or angular velocity of the sample wheel 31 to the speed or angular velocity of the filter wheel 35 is selected equal to the ratio of the number of filters 37 in the filter wheel 35 to the number of compartments 33 in the sample wheel 31. In addition, the number of compartments 33 and the number of filters 37 is selected so that these numbers do not have a common integer divisor. For example, the sample wheel can have 25 compartments arranged equiangularly spaced apart about a circle centered on the axis of rotation, while the filter wheel has nine different filters arranged equiangularly apart on a circle centered about the axis of rotation of the filter wheel. Consequently, the gearing system 39 has a reduction ratio of 25:9 so that the sample wheel 31 rotates at a speed of 360 RPM when the filter wheel is driven at a speed of 1000 RPM. As the sample wheel 31 and the filter wheel 35 are rotated, each of the sample compartments 33 is aligned with each of the filters 37 on the optical path of the photometer.

Filter wheel 35 is secured on a driving shaft 45 of gearing system 39. A pinion 47 is secured on the driving shaft 45 within the gear housing 23. Pinion 47 meshes with a gear wheel 49 secured on an intermediate shaft 51 located laterally from the driving shaft 45. Intermediate shaft 51 is located on the opposite side of the driving shaft 45 from the optical path of the photometer and its axis is parallel to the axis of the driving shaft 45. Sample wheel 31 is fixed on a driven shaft 53 which is powered by a gear belt 55 trained around the intermediate shaft 51. The gear belt 55 runs around a gear belt disc 57 on the driven shaft 53 and around a gear belt disc 59 on the intermediate shaft 51. The gear belt discs 57, 59 are of the same diameter. The axis of driven shaft 53 is parallel with the axis of the driving shaft 45 and of the intermediate shaft 51. Each of these three shafts is rotatably supported in roller bearings 61, 63. A pressure spring 65 is located on each of the shafts for balancing out axial bearing play.

To synchronize the operation of the flash lamp 7 with the rotational position of the sample wheel 31, openings 69 are provided in a flange 67 extending around the outer circumferential periphery of the wheel. These openings are scanned by a light barrier 71. The flash lamp 7 is actuated when a sample compartment 33 is aligned with a filter 37 along the optical path of the photometer.

Figure 2:
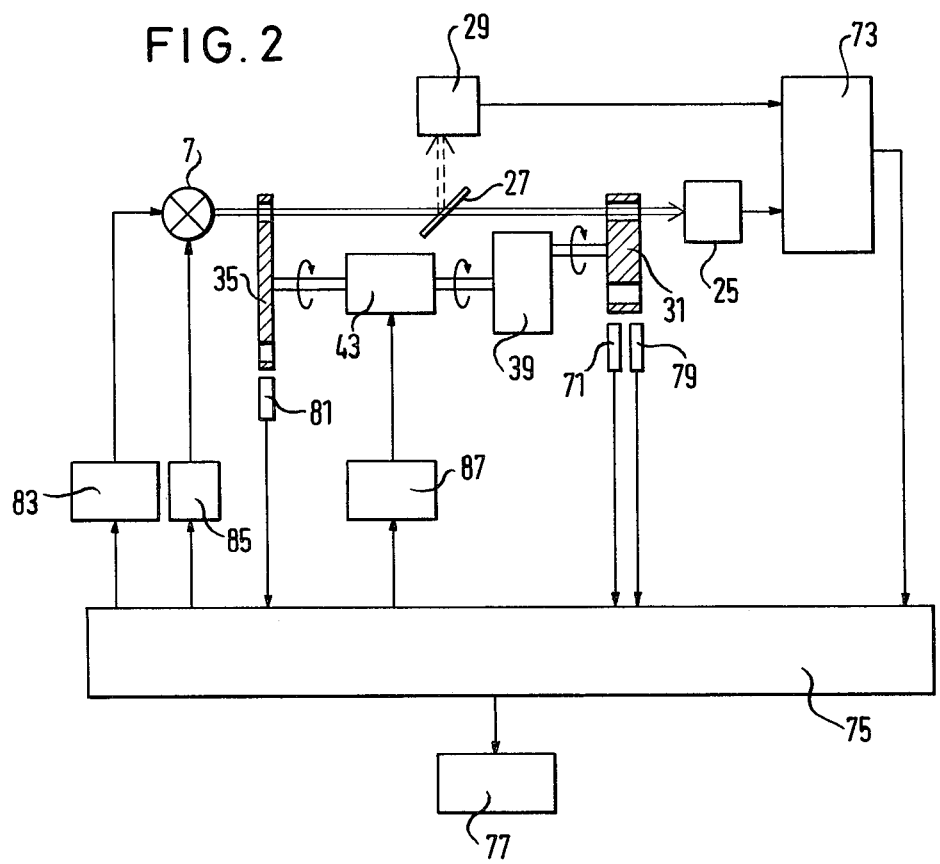
FIG. 2 is a block wiring diagram of the electric design of the photometer shown in FIG. 1.

FIG. 2 shows a wiring diagram of the photometer where the same parts as in FIG. 1 are identified with the same reference numerals. For a description of these parts note the description of FIG. 1. The starting signal for the photo-detector 25, proportional to the intensity of the light of the flash lamp 7 after its passage through a compartment of the sample wheel 31, is conducted to a logarithmic differential amplifier 73 which checks the logarithm of the signal and then reduces it by the logarithm of the signal from the reference photo-detector 29. The starting signal of the logarithmic differential amplifier is conducted by a control circuit 75 to an indicator 77. The indicator 77 displays the absorbance of the sample. Sensors 79, 81 which operate without contact, are assigned to the sample wheel 31 and the filter wheel 35. The sensors release an impulse to the control circuit 75 for each revolution of the sample wheel 31 and the filter wheel 35. The control circuit 75 includes a counter, not shown, whose maximum counting capability is equal to the number of compartments and filters. The counting capability of the counters, assigned to the sample wheel 31 and the filter wheel 35, permit a clear assignment of the measured results to the combinations of individual samples with different filters. Flash lamp 7 is supplied with high voltage by an energy control circuit 83. The energy control circuit 83 is controlled independently of the position of the filter wheel 35 regulated by the control circuit in such a way that the intensity of the light, arriving at the location of the photo-detectors 25, 29, lies within the dynamic range of the photo-detectors regardless of the changing character of the filters. For each filter 37, a control circuit 75 has a setting member at which the power to be delivered by the energy control circuit 83 can be adjusted. Alternatively, the control circuit 75 can have a desired-value storage, connected with the photo-detector 29, so that during a test run in the course of start-up of the photometer a signal, corresponding to the starting signal of the photo-detector 29, can be recorded. During the subsequent measuring operations, the stored signal determines the power to be supplied by the energy control circuit 83. The ignition point of the flash lamp 7 is controlled by a triggering step 85 released by the light barrier 71 and the control circuit 75. The speed of the motor is kept constant by means of a speed controller 87.

In FIG. 3 another embodiment of a polychromatic photometer is illustrated which can be operated with the circuit shown in FIG. 2. The photometer includes a housing 101 containing two vertically extending shafts 103, 105 spaced laterally apart. The shaft 103 extends upwardly out of the housing 101 and supports a sample wheel 107 at its upper end. A gear wheel 113 is secured on the shaft 103 within the housing 101 and between a pair of bearings 109, 111 prestressed in the axial direction. Gear wheel 113 is in meshed engagement with gear wheel 115 fitted on the other shaft 105. Gear wheel 115 is also located within the housing and between a pair of axially prestressed bearings 117, 119. Within the housing 101 below the lower bearing 117, a filter wheel 121 is secured on the shaft 105. An electric motor is connected to the lower end of the shaft 105 via a bevel gearing 123. Sample wheel 107 contains compartments 127 arranged on a circle centered about the axis of the wheel with the compartments equiangularly spaced apart. The filter wheel 121 contains a number of filters 129 arranged on a circle centered on the axis of the shaft 105 with the filters being equiangularly spaced apart. The reduction ratio of the gearing system formed by the gear wheels 113, 115 is dimensioned in accordance with the reduction ratio of the gearing system 39 of the photometer illustrated in FIG. 1.

A flash lamp 133 is located in a chamber 131 within the lower part of the housing 101. A condensing lens 135, firmly secured to the housing, directs light from the lamp 133 emerging from aperture 137 onto one of the filters 129. Since the optical path of the photometric measuring device is located in parallel relation with and spaced between the shafts 103, 105 and is intercepted by the gear wheel 113, openings 139 are provided in the part of the gear wheel 113 which corresponds to the positions of the compartments 127 in the superposed sample wheel 107. Accordingly, light directed upwardly from the lamp 133 passes through the openings 139 for continued upward passage toward the compartments in the sample wheel. To maintain the diameter or size of the openings 139 in the gear wheel 113 as small as possible, a collecting lens 141 is positioned within the housing 101 above the filter wheel 121 and produces an intermediate image in the plane of the gear wheel 113. Above the gear wheel 113 a lens 143 transforms the intermediate image formed in the openings 139 into another intermediate image in the plane of the compartments 127 in the sample wheel 107. A reflecting prism or reflecting mirror 145, located above the sample wheel 107, deflects the light passing along the optical path to another lens 147 located laterally outwardly from the optical path. The light deflected through lens 147 illuminates the measuring surface of a photo-detector 149 located laterally outwardly from the reflecting mirror 145. In the upper portion of the housing 101, above the gear wheel 113, a beam splitter 151 deflects a portion of the light perpendicularly of the plane of FIG. 3 to a reference photometer, not shown. The reflecting mirror 145, the lens 147 and the photo-detector 149 are installed in a head 153 which is rotatably mounted on top of the housing 101 on a shaft 155 disposed in parallel with the shafts 103, 105. In the head 153, additional photo-detectors with appropriate reflecting mirrors and lenses can be installed and positioned in the optical path afforded by the reflecting mirror 45 by rotating the head 153.

As used in this specification and in the claims, the term "common integer" refers to an integer greater than one with the result of the division being a whole number. In other words, the common integer is not evenly divisible into each of the numbers of the sample compartments and of the filters. Based on the example given above, the integers 3 or 9 could be divided evenly into the number of filters, however, they could not be divided evenly into the number of filter compartments, 25. This feature assures the adequate measurement of each sample with each of the filters.

While specific embodiments of the invention have been shown and described in detail to illustrate the application of the inventive principles, it will be understood that the invention may be embodied otherwise without departing from such principles.

What is claimed is:

1. Polychromatic photometer comprising a sample wheel having a plurality of sample compartments therein arranged in a circle with the compartments being equiangularly spaced apart, a filter wheel spaced from said sample wheel and having a plurality of filters therein arranged in a circle with said filters being equiangularly spaced apart, means for rotating said sample wheel about an axis with the axis located in the center of the circle of the sample compartments and for rotating said filter wheel about another axis with the another axis being located in the center of the circle of said filters and each said axis extending normally of the circle within which it is located, a photometric measuring device having an optical path and said rotating means being arranged to bring each of the sample compartments and each of said filters in turn into the optical path of said photometric measuring device, wherein the improvement comprises that said rotating means include a driving device for moving said sample wheel and filter wheel, the number of the sample compartments in said sample wheel being different from the number of said filters in said filter wheel, the number of said sample compartments and of said filters not being divisible by a common integer, and the ratio of angular velocity of said sample wheel to the angular velocity of said filter wheel afforded by said driving device being substantially equal to the ratio of the number of said filters to the number of the sample compartments.

2. Polychromatic photometer, as set forth in claim 1, wherein said driving device comprises a mechanical gearing system for coupling said sample wheel and said filter wheel, and a motor for driving said mechanical gearing system for rotating both said sample wheel and said filter wheel.

3. Polychromatic photometer, as set forth in claim 2, wherein said motor provides a direct drive for said filter wheel, and said gearing system is connected between said filter wheel and said sample wheel.

4. Polychromatic photometer, as set forth in claim 2, wherein said gearing system includes a driving shaft, a driven shaft, and an intermediate shaft, a first gear mounted on said driving shaft, a second gear mounted on said intermediate shaft so that said driving shaft drives said intermediate shaft via said first and second gears, and a belt drive in engagement with said intermediate shaft and said driven shaft for transmitting the driving action from said intermediate shaft to said driven shaft.

5. Polychromatic photometer, as set forth in claim 4, wherein said first gear comprises a first gear wheel secured on said driving shaft, said second gear comprises a second gear wheel secured on said intermediate shaft, and said first and second gear wheels being arranged in meshed engagement.

6. Polychromatic photometer, as set forth in claim 4, wherein said filter drive has a transmission ratio of 1:1.

7. Polychromatic photometer, as set forth in claim 2, wherein said gearing system comprises at least one gear wheel extending transversely of the optical path of said photometric measuring device, said gear wheel having openings therethrough alignable with said sample compartments in said sample wheel and said filters in said filter wheel in the optical path of said photometric measuring device for permitting the passage of light therethrough.

8. Polychromatic photometer, as set forth in claim 7, wherein said photometric measuring device includes a lens located in the optical path thereof for producing an intermediate image in the openings in said gear wheel in a plane transverse of the optical path.

9. Polychromatic photometer, as set forth in claim 7, wherein said gearing system includes a first shaft and a second shaft each rotating about an axis parallel to and spaced laterally from the optical axis of said photometric measuring device, said at least one gear wheel comprises a first gear wheel and a second gear wheel, said sample wheel and said first gear wheel being secured on said first shaft in axially spaced relation, said filter wheel and said second gear wheel being secured on said second shaft in axially spaced relation, and said first and second gear wheels being disposed in meshed engagement.

10. Polychromatic photometer, as set forth in claim 9, wherein said openings for the passage of light being provided in said first gear wheel.

11. Polychromatic photometer, as set forth in claim 2, wherein the axes of rotation of said sample wheel and said filter wheel extend vertically and said sample wheel being located above said filter wheel.

12. Polychromatic photometer, as set forth in claim 1, wherein a counter being provided for each of said sample wheel and said filter wheel for counting the number of rotations of each of said wheels.

13. Polychromatic photometer, as set forth in claim 1, wherein said photometric measuring device includes a flash lamp providing the light source for the measuring operations.

14. Polychromatic photometer, as set forth in claim 13, wherein said photometric measuring device includes an electric energy source with controllable power for supplying power to said flash lamp, and a control element for adjusting the power of said energy source independently of the rotational position of said filter wheel.

15. Polychromatic photometer, as set forth in claim 14, wherein said photometric measuring device includes a reference channel arranged for measuring the intensity of the light from saif flash lamp before the passage of the light through said sample compartments, said control element including a desired-value storage for signals from said reference channel for determining the power of said energy source assigned to the individual said filters of said filter wheel.

* * * * *